(12) United States Patent
Leblanc et al.

(10) Patent No.: US 7,854,925 B2
(45) Date of Patent: *Dec. 21, 2010

(54) USE OF SOLUBILIZED, ANIONIC POLYURETHANES IN SKIN CARE COMPOSITIONS

(75) Inventors: Jean-Pierre Leblanc, Somerville, NJ (US); Mussarat Noor, Roselle Park, NJ (US); Joseph Pasapane, Morristown, NJ (US); Tamara Babenko, Bridgewater, NJ (US)

(73) Assignee: Akzo Nobel N.V., Arnhem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 10/116,368

(22) Filed: Apr. 4, 2002

(65) Prior Publication Data

US 2003/0190294 A1 Oct. 9, 2003

(51) Int. Cl.
A61Q 17/04 (2006.01)
A61Q 19/00 (2006.01)
(52) U.S. Cl. .................. 424/78.03; 424/59; 424/401
(58) Field of Classification Search ............... 424/401, 424/78.03, 78.02
See application file for complete search history.

(56) References Cited

U.S. PATENT DOCUMENTS

| | | | |
|---|---|---|---|
| 5,478,562 A | 12/1995 | Cauwet et al. | |
| 5,626,840 A * | 5/1997 | Thomaides et al. | 424/70.11 |
| 5,658,579 A * | 8/1997 | LaFleur et al. | 424/401 |
| 5,968,494 A | 10/1999 | Kukkala et al. | |
| 5,993,972 A | 11/1999 | Reich et al. | |
| 6,010,686 A * | 1/2000 | De La Poterie et al. | 424/64 |
| 6,039,935 A * | 3/2000 | Mohammadi | 424/59 |
| 6,060,041 A | 5/2000 | Candau et al. | |
| 6,106,813 A | 8/2000 | Mondet et al. | |
| 6,139,829 A * | 10/2000 | Estrin | 424/78.08 |
| 6,228,348 B1 | 5/2001 | Simon et al. | |
| 6,238,654 B1 | 5/2001 | Tournilhac et al. | |
| 6,238,679 B1 | 5/2001 | De la Poterie | |
| 6,245,322 B1 | 6/2001 | Simon | |
| 6,261,578 B1 | 7/2001 | Dupuis | |
| 6,262,299 B1 | 7/2001 | Tsai et al. | |
| 6,264,933 B1 * | 7/2001 | Bodelin et al. | 424/70.7 |
| 6,277,386 B1 | 8/2001 | Kim et al. | |
| 6,291,580 B1 | 9/2001 | Kukkala et al. | |
| 6,342,209 B1 | 1/2002 | Patil et al. | |
| 6,365,697 B1 | 4/2002 | Kim et al. | |
| 6,372,876 B1 | 4/2002 | Kim et al. | |
| 6,395,265 B1 | 5/2002 | Mougin et al. | |
| 6,506,372 B1 | 1/2003 | Dubief et al. | |
| 6,514,488 B1 | 2/2003 | Cauwet-Martin et al. | |
| 2002/0155072 A1 | 10/2002 | Knuppel et al. | |
| 2002/0155079 A1 | 10/2002 | Kim et al. | |
| 2003/0103909 A1 | 6/2003 | Pataut et al. | |

FOREIGN PATENT DOCUMENTS

| | | |
|---|---|---|
| EP | 0 656 021 B1 | 7/1993 |
| EP | 0 779 310 A2 | 6/1997 |
| EP | 0 814 764 B1 | 1/1998 |
| EP | 0 925 774 A2 | 6/1999 |
| EP | 0 937 451 A2 | 8/1999 |
| EP | 1 025 833 A1 | 8/2000 |
| EP | 1 287 809 | 3/2003 |
| EP | 1 306 078 A1 | 5/2003 |
| JP | 11-310699 | 9/1999 |
| JP | 2000-336141 | 12/2000 |
| JP | 2001-39837 | 2/2001 |
| JP | 2001114646 | 4/2001 |
| JP | 2001-172330 | 6/2001 |
| WO | WO 94/03510 | 2/1994 |
| WO | WO 97/25021 | 7/1997 |
| WO | WO99/30674 * | 6/1999 |
| WO | WO 99/65958 | 12/1999 |
| WO | WO 02/070577 | 9/2002 |

OTHER PUBLICATIONS

Modern Pharmaceutics, 3rd Edition, Gilbert Banker, Christopher Rhodes, Marcel Dekker, Chapters 8 (pp. 239-298),15 (pp. 575-609) & 16 (pp. 611-680), New York (1996).

* cited by examiner

*Primary Examiner*—Jyothsna A Venkat
(74) *Attorney, Agent, or Firm*—James C. Abruzzo

(57) ABSTRACT

This patent pertains to the use of anionic polyurethanes in a solubilized state which contribute to enhanced aesthetics to skin care compositions. The polyurethanes may be used alone or in combination with another polymer, particularly acrylate and methacrylate polymers.

6 Claims, No Drawings

USE OF SOLUBILIZED, ANIONIC POLYURETHANES IN SKIN CARE COMPOSITIONS

BACKGROUND OF THE INVENTION

The present invention relates to the use of solubilized, anionic polyurethanes in skin care compositions.

Polyurethanes are known in the art as thickeners for compositions containing surface-active agents and for their use in hair fixative applications. U.S. Pat. Nos. 5,626,840; 5,968,494; and 6,291,580 as well as European Patent Application 99102797.0 (Publication No. EP 0 937 541) all disclose polyurethanes with carboxylate functionality for hair fixative applications.

Polyurethanes are also known for other applications, including cosmetic compositions. However, such polyurethanes are typically formulated in the dispersed state. Polyurethane dispersions are easier to manufacture than solutions. However, dispersed polyurethanes may result in many undesirable properties when formulated in cosmetic formulations. Dispersed polyurethanes are not good film formers, and their use may result in greasy, harsh or uneven feel, long application times, shiny appearance, poor substantivity and/or grittiness.

Other polymers are commonly used in skin care formulas, such as polyacrylates and polymers prepared from alkenes. From a formulator's standpoint, those polymers suffer from the need to heat at elevated temperatures, optionally in the presence of neutralizing agents, to assist in solubilization.

Surprisingly, it has now been discovered that the use of anionic polyurethanes in a solubilized state contribute enhanced aesthetics to skin care compositions without the disadvantages of previously known compositions.

SUMMARY OF THE INVENTION

This patent pertains to the use of anionic polyurethanes in a solubilized state which contribute to enhanced aesthetics to skin care compositions.

DETAILED DESCRIPTION OF THE INVENTION

This patent pertains to the use of anionic polyurethanes in a solubilized state contributing to enhanced aesthetics to skin care compositions.

Any anionic polyurethanes may be used in the skin care compositions of the present invention, including without limitation, those disclosed in U.S. Pat. Nos. 5,626,840; 5,968,494; and 6,291,580 as well as European Patent Application 99102797.0 (Publication No. EP 0 937 541), hereby incorporated by reference. Particularly suitable are anionic polyurethanes, more particularly polyurethanes which incorporate 2,2-hydroxymethyl substituted carboxylic acid. In one embodiment, the polyurethane is limited by the proviso that it not contain a polycondensate of lactic acid.

The polyurethane may be used alone, or in combination with other polymers including, without limitation, acrylate and methacrylate polymers, as well as acrylamide/methacrylamide-based polymers, and polymers derived from other monomers such as maleic anhydride, maleates, butadiene, styrene and its derivatives, vinyl esters, isobutylene, maleimide and substituted maleimides, vinyl amides such as vinyl pyrrolidone and its derivatives, vinyl lactams such as polyvinyl caprolactam, itaconic acids and its esters, alkenes such as eicosene, zwitterionic monomers, cationic monomers such as acrylamidopropyltrimethylammonium chloride and vinylimidazolium chloride. Other combinations include polyesters, polyethers, polyamides, polyesteramides, polyoxazolines, polyols, polyalkylene glycols, other urethane-containing polymers, hydrogels, silicones and silicone-containing copolymers, natural and modified polymers such as cellulose, starches, xanthan, shellac, alginates, guars and other natural and modified gums. A particularly suitable combination is the polyurethane in combination with acrylate and methacrylate polymers, particularly with a poly(meth)acrylate. Such combination may be in any form, including without limitation a simple mixture, a copolymer, or an interpenetrating polymer network.

The polyurethane or polyurethane mixture is solubilized in a suitable solvent using techniques known in the art. Such solvents include without limitation alcohols such as methanol, ethanol, propanol, ethers, esters such as ethyl acetate and propyl acetate, diols such as ethylene glycol, polyols such as glycerol and sorbitol, amides, carbamates, sugars, substituted ethers such as dipropylene glycol dibutyl ether, and non protic polar solvents such as N-methyl pyrrolidone. An advantage of the present polyurethanes is that they do not require thermal energy or long stirring time for solubilization and they may be sold in a dissolved form (solution).

The solubilized polyurethane or polyurethane mixture is advantageous as it may be added directly to the skin care composition without the need for neutralization or may be sold in a neutralized form. In one embodiment of the present invention, the polyurethane is not neutralized.

The solubilized polyurethane or polyurethane mixture may be used in any skin care composition. Such skin care compositions are intended to include without limitation sunscreen and suntan compositions, after-sun compositions, hand and body moisturizers, face creams and lotions, skin tightening and firming compositions, and cleansing compositions, color cosmetics, and whitening compositions.

The solubilized polyurethane or polyurethane mixture is typically present in an amount of at least about 0.1%, more particularly at least about 0.2, most particularly at least about 0.5 and no more than about 15%, more particularly no more than about 10%, most particularly no more than about 5%, by weight of the skin care composition.

Other additives commonly used in skin care compositions may be present in amounts known in the industry. Such additives include without limitation oils, waxes, acidifying or alkalinizing agents, preservatives, active agents, thickeners, emulsifiers, UV agents, emollients, fragrances, antioxidants, odor absorbents, defoamers, lightening agents, pigments, vitamins, botanicals, proteins, enzymes and coenzymes, and colors. In a particularly suitable embodiment, no plasticizer is used.

Yet other additives that can be present in the formulations which can provide therapeutic effects, such as in the treatment of dermatitis hypetiformis, warts, urticaria, hives, scars, keloids, scleroderma, lupus erythematosus, hirsutism, acne, pimples, athlete's foot, herpes, and other conditions as described in *Modern Pharmaceutics*, $3^{rd}$ edition, ed. Gilbert Banker, Christopher Rhodes, Marcel Dekker, New York (1995). As used herein, therapeutic additives will be used to describe such additives.

The resultant skin care compositions have enhanced aesthetics due to the presence of the solubilized anionic polyurethane. Such enhancement may include reduction in greasiness, reduction in gloss, lighter feel, improved smoothness and increased adsorption. The polyurethanes also impart film-forming benefits of importance in moisturizing compositions and stabilizing benefits for colloidal or emulsified systems. Further, the solubilized polyurethane or polyurethane mixture are soluble in aqueous-based formulations and removable by using water or traditional cleansing systems such as soaps and body washes.

The enhanced skin care compositions are applied in the same manner as those known in the art.

EXAMPLES

The following examples are presented to further illustrate and explain the present invention and should not be taken as limiting in any regard. All percents used are on a weight/weight basis.

Example 1

Hand and Body Moisturizing Lotions

A. Polyurethane in the Aqueous Phase

| Ingredients | INCI Designation | % w/w | Supplier |
|---|---|---|---|
| Phase A | | | |
| Carnation White Mineral Oil | Mineral Oil | 10.00 | Penreco |
| Estol 1517 | Isopropyl Palmitate | 6.00 | Uniqema |
| Emersol 132 | Stearic Acid T.P | 2.00 | Emery |
| Cetyl Alcohol | Cetyl Alcohol | 1.00 | |
| Ceralan | Lanolin Alcohol | 0.50 | Amerchol |
| Arlacel 165 | Glyceryl Stearate/PEG-100 Stearate | 3.50 | Uniqema |
| DC 345 | Fluid Cyclomethicone | 1.00 | Dow Corning |
| DC 556 | Fluid Phenyl Trimethicone | 1.00 | Dow Corning |
| Vitamin E Acetate-C | Tocopheryl Acetate | 1.00 | Roche |
| Propylparaben | Propylparaben | 0.10 | |
| Phase B | | | |
| Deionized Water | Water (Aqua) | 65.74 | |
| Triethanolamine (99%) | Triethanolamine | 0.65 | Dow |
| Carbopol Ultrez | Carbopol Ultrez | 0.16 | Noveon |
| Methylparaben | Methylparaben | 0.15 | |
| Trisodium EDTA | Trisodium EDTA | 0.05 | AKZO |
| Phase C | | | |
| Propylene Glycol | Propylene Glycol | 3.00 | |
| Polyurethane/Polyacrylate[1] | Polyurethane (and) polyacrylate copolymer [proposed] | 7.28 | National Starch and Chemical Company |
| Phase D | | | |
| Germall II | Diazolidinyl Urea | 0.15 | Sutton Labs |

[1]Mixture of polyurethane and acrylates copolymer with polyurethane as the major component, 28% solids, 25% ethanol.

Phase B was combined and heated to 80° C. Phase A was combined and heated to 80° C. Phase A was then added to Phase B and mixed for 15 minutes. The mixture was cooled to 40° C. Phase C was combined and added to mixture A/B at 40° C., mixing thoroughly. Phase D was added to mixture A/B/C and mixed until uniform. The mixture was cooled to room temperature.

B. Polyurethane in the Oil Phase

| Ingredients | INCI Designation | % w/w | Supplier |
|---|---|---|---|
| Phase A | | | |
| Mineral Oil | Mineral Oil | 10.00 | Penreco |
| Estol 1517 | Isopropyl Palmitate | 6.00 | Uniqema |
| Emersol 132 | Stearic Acid T.P | 2.00 | Emery |
| Cetyl Alcohol | Cetyl Alcohol | 1.00 | |
| Ceralan | Lanolin Alcohol | 0.50 | Amerchol |
| Polyurethane/polyacrylate[1] | Polyurethane (and) polyacrylate copolymer [proposed] | 7.28 | National Starch and Chemical Company |
| Phase B | | | |
| Deionized Water | Water (Aqua) | 69.05 | |
| Triethanolamine (99%) | Triethanolamine | 0.65 | Dow |
| Carbopol Ultrez | Carbopol Ultrez | 0.16 | Noveon |
| Phase C | | | |
| Phenonip | Phemoxyethanol, Methylparaben, Butylparaben, Ethylparaben, Propylparaben | 0.80 | Nipa |

[1]Mixture of polyurethane and acrylates copolymer with polyurethane as the major component, 28% solids, 25% ethanol.

Phase B was combined and heated to 80° C. Phase A was combined and heated to 80° C. Phase A was added to Phase B and mixed for 15 minutes. Mixture A/B was cooled to 40° C. Phase C was added to mixture A/B at 40° C., mixing until uniform. The mixture was cooled to room temperature.

Example 2

Skin Tightening Emulsion

| Ingredients | INCI Designation | % w/w | Supplier |
|---|---|---|---|
| Phase A | | | |
| Emulgade SE | Glyceryl Stearate, Ethoxylated Cetearylachohol, Cetearyl alcohol, Cetyl palmate | 7.00 | Care Chem |
| Lipoval CO | Castor Oil | 6.00 | Chas Chem |
| Pristerene 4911 | Stearic Acid | 3.00 | Uniqema |
| Prisorine 2040 | Glyceryl Monoisostearate | 2.00 | Uniqema |
| Pricerene 9088 | Glycerin | 2.00 | Uniqema |
| Fancol CB | Cocoa Butter | 1.00 | Fanning |
| Lipovol WGO | Wheat Germ Oil | 1.00 | Lipo |
| Propylparaben | Propylparaben | 0.10 | |
| Phase B | | | |
| Deionized Water | Water (Aqua) | 70.6 | |
| Polyurethane/polyacrylate[1] | Polyurethane (and) polyacrylate copolymer [proposed] | 2.50 | National Starch and Chemical Company |
| FLEXAN ® 130 polymer | Sodium Polystyrene Sulfonate | 2.50 | National Starch and Chemical Company |
| STRUCTURE ® SOLANACE polymeric thickener | Potato starch modified | 2.00 | National Starch and Chemical Company |

-continued

| Ingredients | INCI Designation | % w/w | Supplier |
|---|---|---|---|
| Methylparaben | Methylparaben | 0.15 | |
| Phase C | | | |
| Germall II | Diazolidinyl Urea | 0.15 | |

[1] Mixture of polyurethane and acrylates copolymer with polyurethane as the major component, 28% solids, 25% ethanol.

Phase B was combined and heated to 80° C. Phase A has combined and heated to 80° C. Phase A was added to Phase B at 80° C. and mixed for 15 minutes. The mixture was cooled to 40° C., and Phase C was added, mixing thoroughly. The mixture was cooled to room temperature.

Example 3

Moisturizing Face Cream

A.

| Ingredients | INCI Designation | % w/w | Supplier |
|---|---|---|---|
| Phase A | | | |
| Emulgade SE | Glyceryl Stearate, Ethoxylated Cetearylachohol, Cetearyl alcohol, Cetyl palmate | 7.00 | Care Chem |
| Lipoval CO | Castor Oil | 6.00 | Chas Chem |
| Pristerene 4911 | Stearic Acid | 3.00 | Uniqema |
| Prisorine 2040 | Glyceryl Monoisostearate | 2.00 | Uniqema |
| Pricerene 9088 | Glycerin | 2.00 | Uniqema |
| Fancol CB | Cocoa Butter | 1.00 | Fanning |
| Lipovol WGO | Wheat Germ Oil | 1.00 | Lipo |
| Propylparaben | Propylparaben | 0.10 | |
| Phase B | | | |
| Deionized Water | Water (Aqua) | 72.20 | |
| Polyurethane/polyacrylate[1] | Polyurethane (and) polyacrylate copolymer [proposed] | 5.00 | National Starch and Chemical Company |
| Carbopol 940 | Carbomer | 0.20 | Noveon |
| Triethanolamine (99%) | Triethanolamine | 0.20 | Dow |
| Methylparaben | Methylparaben | 0.15 | |
| Phase C | | | |
| Germall II | Diazolidinyl Urea | 0.15 | |

[1] Mixture of polyurethane and acrylates copolymer with polyurethane as the major component, 28% solids, 25% ethanol.

Phase B was combined and heated to 80° C. Phase A was combined and heated to 80° C. Phase A was added to Phase B at 80° C. and mixed for 15 minutes. The mixture was cooled to 40° C., and Phase C was added, mixing thoroughly. The mixture was cooled to room temperature.

B. Example 3A was repeated except that FLEXAN® 130 polymer was partially substituted for the polyurethane/polyacrylate.

Example 4

Moisturizing Face Lotion

A.

| Ingredient | INCI Designation | % w/w | Supplier |
|---|---|---|---|
| Phase A | | | |
| Arlacel 165 | Glyceryl Stearate, PEG-100 Stearate | 7.00 | Uniqema |
| Finsolv TN | C12-15 Alkyl Benzoate | 6.00 | Finetex |
| Cetyl Alcohol | Cetyl Alcohol | 5.00 | |
| Vitamin E Acetate-C | Tocopheryl Acetate | 1.00 | Roche Vitamins |
| dl-alpha Tocopheryl Acetate | | 1.00 | Roche Vitamins |
| DC 345 | Fluid Cyclomethicone | 1.00 | Dow Corning |
| DC 556 | Fluid Phenyl Trimethicone | 1.00 | Dow Corning |
| Phase B | | | |
| Deionized Water | Water (Aqua) | 74.65 | |
| Carbopol 940 | Carbomer | 0.20 | Noveon |
| Triethanolamine (99%) | Triethanolamine | 0.20 | Dow |
| Versene 100 | Tetrasodium EDTA | 0.15 | Dow Chemical |
| Phase C | | | |
| Polyurethane/polyacetate | Polyurethane (and) polyacrylate copolymer [proposed] | 2.00 | National Starch and Chemical Company |
| Phenonip | Phenoxyethanol, Methylparaben, Butylparaben, Ethylparaben, Propylparaben | 0.80 | Nipa |

[1] Mixture of polyurethane and acrylates copolymer with polyurethane as the major component, 28% solids, 25% ethanol.

Phase B was combined and heated to 80° C. Phase A was combined and heated to 80° C. Phase A was added to Phase B at 80° C. and mixed for 15 minutes. The mixture was cooled to 40° C., to which Phase C was added, and mixed until uniform. The mixture was cooled to room temperature.

Example 5

Sunscreen Emulsion

A.

| Ingredient | INCI Designation | % w/w | Supplier |
|---|---|---|---|
| Phase A | | | |
| Finsolv TN | C12-15 Alkyl Benzoate | 6.00 | Finetex |
| Neo Heliopan OS | Octyl Salicylate | 5.00 | H & R |
| Neo Heliopan AV | Ethylhexyl Methoxycinnamate | 7.50 | H & R |
| Neo Heliopan BB | Benzophenone-3 (Oxybenzone) | 4.00 | H & R |
| Parsol 1789 | Butyl Methoxydibenzoylmethane (Avobenzone) | 1.60 | Roche |

-continued

| Ingredient | INCI Designation | % w/w | Supplier |
|---|---|---|---|
| Tego Care 450 | Polyglyceryl-3 Methylglucose Distearate | 3.00 | Goldschmidt |
| Syncrowax ERL-C | C18-36 Acid Glycol Ester | 0.60 | Croda |
| DC 200 Fluid, 10 CST | Dimethicone | 3.00 | Dow Corning |
| Vitamin E Acetate | Tocopheryl Acetate | 0.10 | Roche |
| Phase B | | | |
| Deionized Water | Water (Aqua) | 20.00 | |
| Carbopol EDT 2020 | Acrylates/C10-30 Alkyl Acrylate Crosspolymer | 0.18 | Noveon |
| Versene 100 | Tetrasodium EDTA | 0.15 | Dow Chemical |
| Phase C | | | |
| 1,4 Butanediol | Butylene Glycol | 4.00 | BASF |
| TEA 99% | Triethanolamine | 0.18 | Union Carbide |
| Deionized Water | Water (Aqua) | 41.11 | |
| Polyurethane/polyacrylate | Polyurethane (and) polyacrylate copolymer [proposed] | 7.28 (2.0% dry basis) | National Starch and Chemical Company |
| Phase D | | | |
| TEA 99% | Triethanolamine | 0.08 | Union Carbide |
| Phase E | | | |
| Phenonip | Phenoxyethanol, Methylparaben, Butylparaben, Ethylparaben, Propylparaben | 0.80 | Nipa |

[1]Mixture of polyurethane and acrylates copolymer with polyurethane as the major component, 28% solids, 25% ethanol.

The first three ingredients of Phase A were combined and mixed well. Neo Heliopan BB was added and mixed at room temperature for 10 minutes. While mixing, the mixture was heated to 80° C. Parsol 1789 was added and mixed for 5 more minutes while keeping temperature at 80° C. Tego Care 450 was added and mixed 2-3 minutes. Syncrowax ERL-C was added and mixed for another 2-3 minutes. The remaining ingredients of Phase A are added and mixed, keeping the temperature of Phase A at 80° C.

In a separate vessel, Carbopol EDT2020 was sifted in room temperature deionized water and mixed while heating to 75°-80° C. Versene 100 was added when Carbopol EDT2020 was completely dispersed.

Butylene Glycol and TEA were premixed and the polyurethane/polyacrylate was added. The deionized water of Phase C was heated to 85° C. then added to the other components of phase C at 85° C. Phase C was mixed for 5 minutes while keeping temperature at 80-85 C.

Phase A was slowly added to Phase B. Phase D was then added to mixture A/B until a pH of 6.5-6.6 is reached and mixed well. High shear mixing was applied and Phase C was added to mixture A/B/D at a temperature of 80-85° C. Phase E was added at a temperature of no more than 55° C. While cooling to 30° C., moderate mixing was applied. The mixture was then homogenized (~9,000 rpm) at 30° C. for 3-5 minutes. The water loss was calculated and added back in to the mixture.

B. Example 5A was repeated except that the amount of polyurethane/polyacrylate used was 3.64% w/w (1.0% on a dry weight basis) and water was added to make up the weight.

C. Example 5A was repeated except that 2.00% w/w DERMACRYL® polymer (commercially available from National Starch and Chemical Company) was added in Phase C and the polyurethane/polyacrylate was not used.

A subjective sensory panel (8 panelists) compared Samples 5A and 5C with the following results shown in Table 1:

TABLE 1

| Sample | Example 5A | Example 5C |
|---|---|---|
| Smooth/soft | 5/8 | 3/8 |
| Greasy | 1/8 | 7/8 |
| Quick absorption | 7/8 | 1/8 |
| Tacky | 0/8 | 8/8 |
| Drag | 2/8 | 6/8 |
| Gloss | 1/8 | 7/8 |
| Light Feel | 4/8 | 4/8 |
| After feel | 5/8 | 3/8 |

Table 1 shows that the polyurethane/polyacrylate sample is significantly less greasy, less tacky, less shiny and is more quickly absorbed than the comparative example.

D. Example 5A was repeated except that the polyurethane/polyacrylate was omitted and in Phase C, 0.63% w/w TEA was used. Sample 5A provided improved afterfeel after a gentle water rinse.

Samples D (control), A (2% polyurethane acrylate, dry basis), and C (2% Dermacryl, dry basis) were evaluated for in-vitro SPF efficiency. The control was found to confer a SPF of 36, as compared to 53 for sample A and 65 for sample C, demonstrating the film-forming behavior of solution polyurethanes.

Example 6

Sunscreen Emulsions

A.

| Ingredient | INCI Designation | % w/w |
|---|---|---|
| Phase A | | |
| Water | Water, deionized | 75.70 |
| Versene 100 | Tetrasodium EDTA | 0.20 |
| Princerine 9088 | Glycerine | 2.00 |
| Carbomer | Carbopol 940 | 0.20 |
| Phase B | | |
| Hall Brite TQ | Diethylhexyl naphthalate | 3.10 |
| Neo Heliopan AV | Octyl Methoxycinnamate | 3.10 |
| Neo Heliopan OS | Octyl Salicylate | 3.50 |
| Parsol 1789 | Butyl Methoxydibenzoylmethane | 2.00 |
| Dow 193 | Dimethicone Copolymer | 1.00 |
| Dow 200/100 cps | Dimethicone | 1.00 |
| Brij 721 | Steareth-21 | 0.80 |
| Brij 72 | Steareth-2 | 1.00 |
| Arlacel 165 | Glyceryl Stearate (and) PEG-100 Stearate | 1.20 |
| Phenonip | Phenoxyethanol, methylparaben, ethylparaben, propylparaben, butylparaben | 1.00 |

-continued

| Ingredient | INCI Designation | % w/w |
|---|---|---|
| Phase C | | |
| Water | Water | 0.00 |
| TEA (99%) | Triethanolamine | 0.20 |
| Phase D | | |
| Polyurethane (and) polyacrylate copolymer [proposed] | Polyurethane/polyacrylate | 4.00 |

[1]Mixture of polyurethane and acrylates copolymer with polyurethane as the major component, 28% solids, 25% ethanol.

Water, Tetrasodium EDTA and Glycerin of Phase A were combined at room temperature. Carbomer was slowly sprinkled onto the surface while stirring. After incorporating all the Carbomer, Phase A was heated to 80° C. Phase B was prepared separately, heated to 80° C. and stirred until uniform. Phase B was slowly added to Phase A with mixing. When the mixture appeared uniform, Phase C was added with mixing. After achieving uniformity again, the heat was turned off and mixing was switched to sweep. Sweep mixing was continued throughout cool-down. Phase D was added with stirring at 45° C. Water was added to make up for loss during heating and stirred to room temperature.

B. Example 6A was repeated except that water was substituted for the polyurethane/polyacrylate.

Both samples produced a smooth, rich, white-colored emulsion. The samples were tested for SPF and water resistance using the following methodology.

Instrumentation:

A Labsphere UV1000S Ultraviolet Transmittance Analyzer was used to determine the absorbence spectra of the samples.

Substrate:

Vitro-Skin®—the skin was hydrated prior to use. Pieces of the Vitro-Skin® were cut to fit the slide mounts being used. A small hydration chamber was used. Approximately 200 ml of hydrating solution (30% glycerin in distilled water) were added to the chamber. The chamber was sealed and kept at a temperature of approximately 23° C. for sixteen (16) hours. This provided the recommended humidity atmosphere for hydration of the Vitro-Skin®. After Sixteen (16) hours, the skin was ready for use. Test materials were applied to the rough side of the Vitro-Skin®.

Five samples of substrate were used for each sample. One reference sample was also be prepared.

The substrate was placed on a balance and a 2 mg/cm$^2$ portion of the sample was applied using a syringe with a fine blunt needle. The substrate was removed from the balance and transferred to a foam block to simulate the flexibility of human dermis. The sample was distributed on the substrate by dotting the sunscreen on and noting the weight. The sunscreen-coated substrate was removed from the balance and spread evenly over the site using a fingercot for 20-30 strokes (approximately 20 seconds).

After product application, the samples were allowed to dry for at least 15 minutes to let the emulsion break down. A blank (no sunscreen applied) substrate will serve as the reference untreated control.

Measurements:

Measurements were performed using the Labsphere UV-1000S Ultraviolet Transmittance Analyzer. A baseline scan was performed using the reference sample. A second scan of the reference sample was run.

The results demonstrated a flat baseline at 100% ±0.5%.

Measurements for the sunscreen-substrate were then performed. Five measurements per sample were performed at various spots on the sample to ensure proper spreading of the test material.

Water-Resistant

METHODOLOGY: The Vitro-Skin® was immersed in a water bath for forty (40) minutes. After the dry time, the sunscreen-substrate preparation was insulted with a full spectrum UV dose corresponding to 1 MED times ⅓ the test material SPF value. It was calculated as follows:

$$UV\ Dose = \frac{SPF}{3} \times 1\ J/cm^2$$

Very Water-Resistant

METHODOLOGY: The Vitro-Skin® was immersed in a water bath for eighty (80) minutes. After the dry time, the sunscreen-substrate preparation was insulted with a full spectrum UV dose corresponding to 1 MED times ⅓ the test material SPF value. It was calculated as follows:

$$UV\ Dose = \frac{SPF}{3} \times 1\ J/cm^2$$

TABLE 2

| Polymer | Level-solids | Mean SPF | WR* SPF | VWR* SPF |
|---|---|---|---|---|
| Sample 6A | 1 | 29.47 | 10.25 | 9.87 |
| Sample 6B | 0 | 26.07 | 1.78 | |

WR* SPF - water resistant SPF, 40 min immersion
VWR* SPF - very water resistant SPF, 80 min immersion As can be seen from Table 2, the use of the polyurethane/polyacrylate added SPF protection as well as water resistance.

Example 7

Water Resistant Sunscreen

| Ingredient | Amount (% w/w) |
|---|---|
| Phase A | |
| SDA-40 (Ethanol) | 71.50 |
| Polyurethane | 8.00 (2.0% solids) |
| Phase B | |
| C$_{12-15}$ Alkyl Benzoate | 7.50 |
| Octyl Methoxycinnamate | 5.00 |
| Octyl Salicylate | 5.00 |
| Butyl Methoxydibenzoylmethane | 3.00 |

Phase B ingredients were combined and heated to 75° C. while mixing. The mixture was cooled to room temperature and premixed Phase A was added.

Example 8

Sunscreen with Emulsified Polyurethane

| Ingredient | Amount (% w/w) |
|---|---|
| Phase A | |
| Octyl Methoxycinnamate | 7.50 |
| Octyl Salicylate | 5.00 |
| Isopropyl Palmitate | 5.00 |
| Polyurethane | 8.00 (2.0% solids) |
| Phase B | |
| D.I. Water | 73.50 |
| Preservatives | 1.00 |

Phase A ingredients were premixed. Phase B ingredients were premixed and slowly added to Phase A while homogenizing. A white, thin emulsion formed.

Example 9

Moisturizing Lotion

| Ingredient | Amount (% w/w) |
|---|---|
| Phase A: | |
| C12-15 Alkyl Benzoate | 25.00 |
| Polyurethane | 6.70 (1.675% solids) |
| Phase B | |
| D.I. Water | 68.30 |
| Preservatives | 1.00 |

Phase A ingredients were mixed well. Phase B ingredients were mixed and slowly added to Phase A. The mixture was homogenized.

We claim:

1. A skin care composition comprising an aqueous-based formulation of a mixture of a preneutralized, solubilized anionic polyurethane and a solubilized poly(meth)acrylate polymer, wherein the amount of preneutralized, solubilized anionic polyurethane and poly(meth)acrylate is 5 wt % or less by weight of the composition and wherein the polyurethane and the poly(meth)acrylates provide both SPF protection and water resistance; and at least one solvent, wherein the composition has enhanced aesthetics on skin, wherein the composition is less greasy, less tacky, less shiny and absorbed faster than a skin care composition without the polyurethane, and wherein the composition is in the form of an emulsion or a colloid.

2. The composition of claim 1 wherein the poly(meth)acrylate is polyacrylate.

3. The composition of claim 1 wherein the skin care composition is selected from the group consisting of sunscreens, suntan compositions, after-sun compositions, hand moisturizers, body moisturizers, face creams, face lotions, skin tightening compositions, skin firming compositions, skin cleansing compositions, color cosmetics, and whitening compositions.

4. The composition of claim 1 wherein the amount of preneutralized, solubilized anionic polyurethane and poly(meth) acrylate is about 0.1 wt % to 5 wt % by weight of the composition.

5. The composition of claim 4, wherein the amount of preneutralized, solubilized anionic polyurethane and poly(meth) acrylate is about 0.2 wt % to 5 wt % by weight of the composition.

6. The composition of claim 4, wherein the amount of preneutralized, solubilized anionic polyurethane and poly(meth) acrylate is about 0.5 wt % to 5 wt % by weight of the composition.

* * * * *